United States Patent
Tsuji et al.

(10) Patent No.: US 6,893,875 B2
(45) Date of Patent: May 17, 2005

(54) METHOD FOR ASSAY OF ANALYTE BY ADJUSTMENT OF CHEMILUMINESCENCE

(75) Inventors: Yasuhiro Tsuji, Tokyo (JP); Keiichi Kamisango, Tokyo (JP); Mitsuo Otsuka, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/307,721

(22) Filed: May 10, 1999

(65) Prior Publication Data

US 2002/0042146 A1 Apr. 11, 2002

Related U.S. Application Data

(62) Division of application No. 08/875,592, filed as application No. PCT/JP96/00218 on Feb. 2, 1996, now Pat. No. 5,952,238.

(30) Foreign Application Priority Data

Feb. 2, 1995 (JP) .............................................. 7-51668

(51) Int. Cl.[7] .............................................. G01N 21/76
(52) U.S. Cl. .......................... 436/172; 436/27; 436/56; 436/164; 436/501; 436/546; 436/800; 436/805; 436/825; 435/6; 435/7.1; 435/7.93; 435/91.2; 422/52; 422/68.1; 422/82.05
(58) Field of Search ............................. 435/6, 7.1, 7.2, 435/7.92, 7.93, 7.94, 7.95, 91.2, 960, 962, 968; 436/27, 56, 164, 172, 501, 546, 800, 824, 825; 422/52, 68.1, 82.05

(56) References Cited

U.S. PATENT DOCUMENTS

| | | |
|---|---|---|
| 3,734,449 A | 5/1973 | Itou et al. |
| 3,996,345 A | 12/1976 | Ullman et al. |
| 4,220,450 A | 9/1980 | Maggio |
| 4,645,646 A | 2/1987 | Gadow et al. |
| 5,017,473 A | 5/1991 | Wagner |
| 5,034,314 A | 7/1991 | Geiger et al. .................. 435/6 |
| 5,059,790 A | 10/1991 | Klaimer et al. |
| 5,082,768 A | 1/1992 | Burd et al. |
| 5,302,467 A | 4/1994 | Baumgartner et al. |
| 5,315,993 A | 5/1994 | Aleale |
| 5,332,662 A | 7/1994 | Ullman |
| 5,388,803 A | 2/1995 | Baumgartner et al. |
| 5,487,972 A | 1/1996 | Gelford et al. |
| 5,639,604 A * | 6/1997 | Arnold et al. ............. 436/7.92 |
| 5,952,238 A * | 9/1999 | Tsuji et al. .................. 436/172 |

FOREIGN PATENT DOCUMENTS

| | | |
|---|---|---|
| CA | 1125632 | 6/1982 |
| CA | 1174166 | 9/1984 |
| EP | 0034952 A2 | 9/1981 |
| EP | 0063852 A2 | 11/1982 |
| EP | 0165072 A2 | 12/1985 |
| EP | 0343346 A1 | 11/1989 |
| JP | 235359 A | 2/1990 |

OTHER PUBLICATIONS

Arnold et al., Clin. Chem., vol. 35, No. 8 (1989) pp. 1588–1594.

* cited by examiner

*Primary Examiner*—Chris Chin
*Assistant Examiner*—Gailene R. Gabel
(74) *Attorney, Agent, or Firm*—Birch, Stewart, Kolasch & Birch, LLP

(57) ABSTRACT

A method for assay of an analyte by use of a material labeled with a chemiluminescent substance, which comprises adding a quencher and/or decreasing the specific activity of a chemiluminescent substance labeled probe, thereby decreasing the quantity of chemiluminescence.

6 Claims, 2 Drawing Sheets

METHOD FOR ASSAY OF ANALYTE BY ADJUSTMENT OF CHEMILUMINESCENCE

This application is a divisional of application Ser. No. 08/875,592, filed on Oct. 8, 1997, now U.S. Pat. No. 5,952,238. Application Ser. No. 08/875,592 is the national phase of PCT International Application No. PCT/JP96/00218 filed on Feb. 2, 1996 under 35 U.S.C. § 371. The entire contents of each of the above-identified applications are hereby incorporated by reference.

TECHNICAL FIELD

This invention relates to a method for assay of an analyte by use of a material labeled with a chemiluminescent substance. More specifically, the invention relates to a method for assay in a broader range by decreasing the quantity of chemiluminescence.

BACKGROUND ART

Among methods for assay of an analyte in a test solution is one using a probe labeled with a chemiluminescent substance. This method is widely used as being capable of determining the amount of the analyte highly sensitively by measuring the quantity of chemiluminescence. This method is useful for a suitable amount of the analyte. In the presence of a large amount of the analyte (e.g. when many copies are produced by gene amplification such as polymerase chain reaction), however, the quantity of chemiluminescence by the method exceeds the determination limit of a measuring device, making accurate assay impossible. Such samples with results in excess of the upper assay limit have been determined again after dilution of the test solution. This procedure is very laborious. Samples amplified by gene amplification, in particular, can cause contamination of the amplified product as a result of dilution. Utmost care has been taken to avoid the contamination, further increasing labor. To broaden the range of assay without diluting the sample, there has been no choice but to wait for an improvement in the measuring device.

We, the inventors, have found that the foregoing problems with the determination of a sample beyond the assay limits can be solved by decreasing the quantity of chemiluminescence, without requiring a laborious operation such as the dilution of the sample, or an improvement in the measuring device. This finding has led us to accomplish this invention.

DISCLOSURE OF THE INVENTION

The present invention is a method for assay of an analyte by use of a material labeled with a chemiluminescent substance, which comprises decreasing the quantity of chemiluminescence. The invention further provides a method for assay which comprises adding a quencher and/or decreasing the specific activity of a chemiluminescent substance labeled probe.

The assay of the analyte by use of a material labeled with a chemiluminescent substance, indicated above, refers, for example, to reacting a sample containing an analyte with a material labeled with a chemiluminescent substance, and measuring the quantity of chemiluminescence of the conjugate to detect or determine the analyte.

Figure 1:
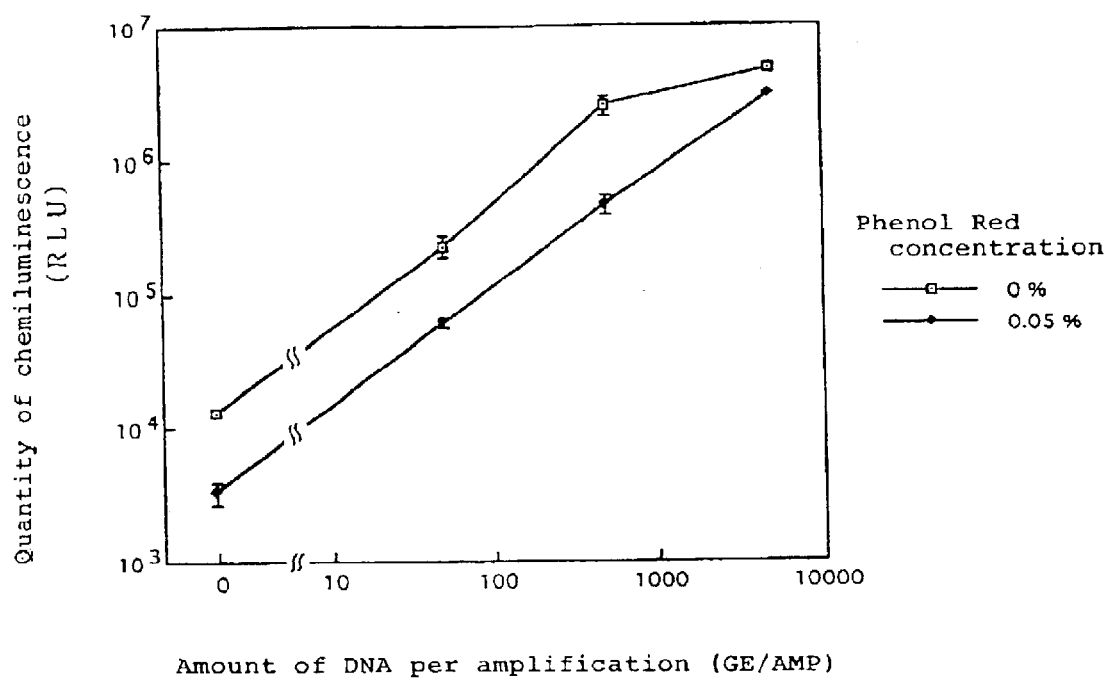
FIG. 1 shows the effect of Phenol Red addition on the quantitative amplification and detection of HBV template in the serum.

BEST MODE FOR CARRYING OUT THE INVENTION (1) Decreasing the Quantity of Chemiluminescence by Addition of a Quencher The quencher used in the present invention may be any substance which can quench chemiluminescence. For example, it includes color matters and india ink (drops of india ink, supernatant of india ink). Examples of the color matters are Crystal Violet, Bromophenol Blue, carminic acid, Chlorophenol Red, hematoxylin, Bromophenol Purple, Bromophenol Red, rosolic acid, Phenol Red, Cresol Red, and Methacresol Red.

When the color matter is used as the quencher, the concentration of the color matter at measurement of chemiluminescence may be in the range of 0.01 to 10%, preferably 0.01 to 1%, although it differs depending on the color matter used. When india ink is used as the quencher, on the other hand, its amount at measurement of chemiluminescence may be in the range of 0.01 to 50%, preferably 1 to 20%, based on the amount of the test solution. The quencher may be added at any time before measurement of chemiluminescence. For example, it may be added either before or after the reaction between the analyte and the labeled probe.

(2) Decreasing the Quantity of Chemiluminescence by Decreasing the Specific Activity of a Chemiluminescent Substance Labeled Probe To decrease the specific activity of a labeled probe in the present invention, an unlabeled probe is added to the labeled probe. The unlabeled probe may be added in an amount in the range of 0.1 to $10^5$, preferably 10 to $10^3$, with respect to 1 of the labeled probe.

(3) Combining the Method (1) and the Method (2)

In the present invention, the addition of the quencher and the reduction of the specific activity of the chemiluminescent substance labeled probe may be combined. The conditions for use of both methods in this combination follow the above-described ranges.

The use of the assay method according to the present invention enables the quantity of chemiluminescence to be measured accurately, even when the analyte in the sample solution is present in so large an amount as to exceed the assay limit. For instance, the analyte can be easily detected or determined quantitatively from a product produced by gene amplification of genetic information (DNA or RNA) on a microorganism or cell. This action can be confirmed by Examples 1 to 4 to be offered later on.

In the method involving the addition of the quencher, not only positive signals, but also background (noise) levels are decreased. This decrease in the quantity of chemiluminescence permits the quantitative measurement of strongly positive signals, while the decrease in the background (noise) levels makes discrimination of weakly positive signals possible. In short, the addition of the quencher enables the assay of a highly positive sample without affecting the determination of a weakly positive sample. This action can be confirmed by Examples 1 to 3 to be offered later on.

By using the present invention to decrease the quantity of chemiluminescence, it becomes possible to detect or quantitatively determine a highly positive sample or a sample beyond the assay limits. The method of adding the quencher, in particular, reduces the background (noise) level as well. Thus, a highly positive sample can be measured without influence on the assay of a weakly positive sample. Hence, the method of the present invention proves to be an excellent method which can broaden the range of assay without diluting the sample or improving the measuring device.

EXAMPLES

The present invention will now be described in more detail with reference to Examples, whose descriptions do not limit the invention.

Example 1

Method

Five μl of human serum containing HBV-DNA sequence (Galibert, F., Mandart, E., Fitioussi, F., Tiollais, P. and Charnay, P., Nature 281, 646–650 (1979)) (50 to 5,000 copies per amplification) was mixed with 20 μl of an alkaline solution (pH 13), followed by heating for 5 minutes at 97° C. At room temperature, the mixture was allowed to cool for 10 minutes, and then neutralized with a buffer. Two kinds of primer were added, and annealing was performed at room temperature. After DNA and RAN polymerases were added, gene amplification (using the method described in Officially Published Japanese Patent Gazette No. 500759/92) was carried out at 37° C. The amplification product and an acridinium ester labeled probe were hybridized at 60° C.; whereafter the amplification product was detected by the HPA method (Arnold JR, L. J., Hammond, P. W., Wiese, W. A. and Nelson, N. C., Clinical Chemistry 35, 1588–1594 (1989)). In detecting the amplification product by the measurement of chemiluminescence, the effect of addition of Phenol Red was investigated. Phenol Red was added in an amount of 0.05% to test a solution for chemiluminescence measurement to measure the quantity of chemiluminescence. The results of measurement were compared with the results obtained from the testing solution containing no Phenol Red. The results are shown in FIG. 1.

Discussion

As shown in FIG. 1, the Phenol Red-free sample nearly reached the assay limit (saturation value) at about 500 GE (genome equivalents)/AMP, above which the quantity of chemiluminescence became no more linear. With the Phenol Red-containing sample, the quantity of chemiluminescence remained linear even at 5,000 GE/AMP. This means that the addition of Phenol Red made the assay of 500 GE/AMP or more possible. Compared with the Phenol Red-free sample, the Phenol Red-containing sample markedly reduced the background (noise) level (DNA content=0), thus permitting the assay of a weakly positive sample (about 50 GE/AMP). In other words, the addition of Phenol Red enabled the assay of a highly positive sample without affecting the determination of a weakly positive sample.

Example 2

Method

In detecting the amplification product obtained by gene amplification as in Example 1, various amounts of Phenol Red were added to study the effect of Phenol Red addition. Phenol Red was added in an amount of 0.025 to 0.2% to a test solution for chemiluminescence measurement to measure the quantity of chemiluminescence. The results of measurement were compared with the results obtained using the testing solution containing no Phenol Red. The results are shown in Table 1.

TABLE 1

Effect of Phenol Red at determination of quantity of chemiluminescence

| Phenol Red concentration (%) | Positive sample (50 GE/AMP) | Negative sample (0 GE/AMP) | Positive/ negative ratio |
| --- | --- | --- | --- |
| 0 | 237340 | 967 | 245 |
| 0.025 | 73120 | 239 | 306 |
| 0.05 | 41706 | 172 | 242 |
| 0.1 | 19332 | 114 | 170 |
| 0.2 | 7571 | 89 | 85 |

Discussion

As shown in Table 1, the quantity of chemiluminescence from the positive sample and the quantity of chemiluminescence (background) from the negative sample decreased in a manner dependent on the amount of Phenol Red added. These findings demonstrate that the inventive method is available in a wide range of phenol Red concentrations.

Example 3

Method

Tests were conducted in the same way as in Example 2, except that commercially available india ink was used instead of Phenol Red.

To a test solution for chemiluminescence measurement, 1.25 to 10% by volume of india ink was added, and the quantity of chemiluminescence was measured. The results are shown in Table 2 in comparison with the results of measurement of the test solution free from india ink.

TABLE 2

Effect of india ink at determination of quantity of chemiluminescence

| Amount of india ink added (% by volume) | Positive sample (50 GE/AMP) | Negative sample (0 GE/AMP) | Positive/ negative ratio |
| --- | --- | --- | --- |
| 0 | 291638 | 1689 | 173 |
| 1.25 | 30902 | 218 | 142 |
| 2.5 | 21292 | 119 | 179 |
| 5 | 6609 | 63 | 105 |
| 10 | 5172 | 43 | 120 |

Discussion

As shown in Table 2, the quantity of chemiluminescence from the positive sample and the quantity of chemiluminescence (background) from the negative sample decreased in a manner dependent on the amount of india ink added. These findings demonstrate that the inventive method can be used in a wide range of india ink concentrations.

Example 4

Method

Gene amplification was performed in the same manner as in Example 1. When the amplification product and an acridinium ester labeled probe were hybridized at 60° C., an unlabeled probe in various amounts was added. The amounts of the unlabeled probe were 10 to 1,000 relative to 1 of the labeled probe. After hybridization, the quantities of chemiluminescence in the samples were measured by the HPA method. The results are shown in FIG. 2 in comparison with the results of measurement of the test solution free from the unlabeled probe.

Discussion

Figure 2:
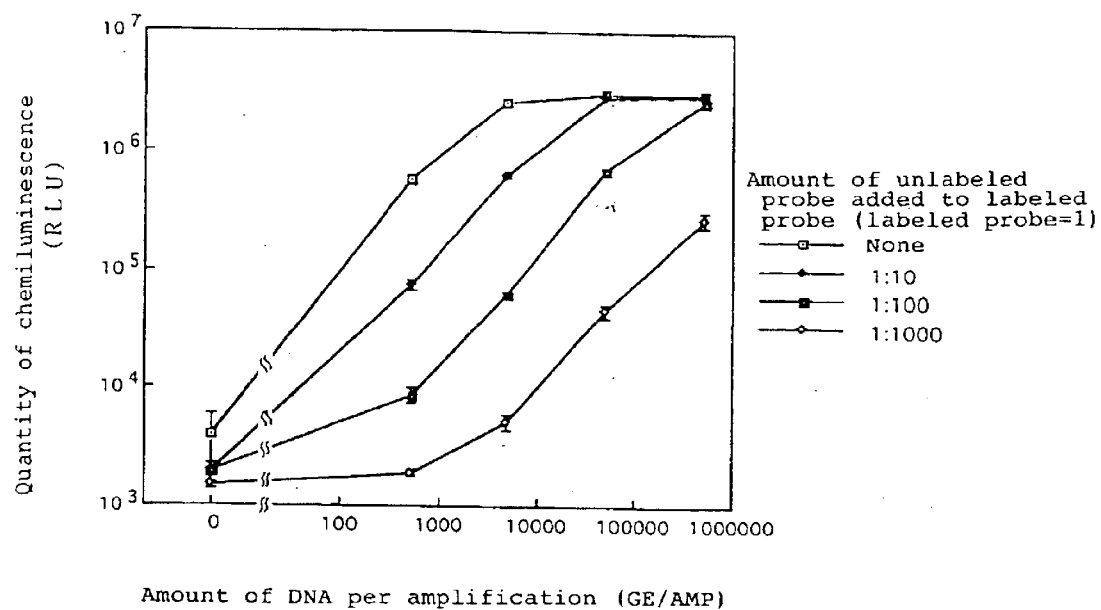
FIG. 2 shows the effect of unlabeled probe addition on the quantitative amplification and detection of HBV template in the serum.

As shown in FIG. 2, the unlabeled probe-free sample nearly reached the assay limit (saturation value) at about 500 to 5,000 GE/AMP, above which the quantity of chemiluminescence became no more linear. The unlabeled probe-containing samples, on the other hand, showed decreases in the quantity of chemiluminescence in a manner dependent on the amount of the unlabeled probe added. When the amount of the unlabeled probe added relative to the labeled probe was 100(unlabeled probe):1(labeled probe) or more, assay was possible even at about 500,000 GE/AMP. Thus, the addition of the unlabeled probe permitted assay of 500 to 500,000 GE/AMP or more.

What is claimed is:

1. A method for assay of an analyte which is an amplified gene product which comprises:
   (1) providing in a test solution a first probe that specifically hybridizes to said analyte, wherein said first probe is labeled with a chemiluminescent substance and said analyte comprises an amplified gene product;
   (2) adding to said test solution after said first probe has bound to said analyte, an unlabeled, second probe that competes with said first probe for specifically hybridizing to said analyte, wherein the ratio of unlabeled probe to labeled probe is $0.1–10^5$ to 1;
   (3) quantitatively measuring a chemiluminescent signal, wherein said second unlabeled probe competes with said first probe for said analyte and results in signal quenching by physical reduction in the number of molecules of the first probe bound to the analyte; and
   (4) correlating said chemiluminescence to the presence of said analyte.

2. The method of claim 1, wherein said unlabeled probe is added in an amount of from 10 to $10^3$ parts per one part of the labeled probe.

3. A method for assay of an analyte which is an amplified gene product which comprises:
   (1) providing in a test solution a first nucleic acid probe that specifically hybridizes to said analyte, wherein said first probe is labeled with a chemiluminescent substance and said analyte comprises an amplified gene product;
   (2) adding to said test solution after said first probe has bound to said analyte, an unlabeled, second nucleic acid probe that competes with said first probe for specifically hybridizing to said analyte, wherein the ratio of unlabeled probe to labeled probe is $0.1–10^5$ to 1;
   (3) quantitatively measuring a chemiluminescent signal, wherein said second unlabeled probe competes with said first probe for said analyte and results in signal quenching by physical reduction in the number of molecules of the first probe bound to the analyte; and
   (4) correlating said chemiluminescence to the presence of said analyte.

4. A method for assay of an analyte which is an amplified gene product which comprises:
   (1) providing in a test solution a first probe that specifically hybridizes to said analyte and a second probe that competes with said first probe for specifically hybridizing to said analyte, wherein said first probe is labeled with a chemiluminescent substance and said second probe is unlabeled, and wherein said analyte comprises an amplified gene product, wherein the ratio of unlabeled probe to labeled probe is $0.1–10^5$ to 1;
   (2) quantitatively measuring a chemiluminescent signal using HPA (hybridization protection assay), wherein said second unlabeled probe competes with said first probe for said analyte and results in signal quenching by physical reduction in the number of molecules of the first probe bound to the analyte; and
   (3) correlating said chemiluminescence to the presence of said analyte.

5. The method of claim 4, wherein said unlabeled probe is added in an amount of from 10 to $10^3$ parts per one part of the labeled probe.

6. A method for assay of an analyte which is an amplified gene product which comprises:
   (1) providing in a test solution a first nucleic acid probe that specifically hybridizes to said analyte and a second nucleic acid probe that competes with said first nucleic acid probe for specifically hybridizing to said analyte, wherein said first nucleic acid probe is labeled with a chemiluminescent substance and said second nucleic acid probe is unlabeled, and wherein said analyte comprises an amplified gene product, wherein the ratio of unlabeled probe to labeled probe is $0.1–10^5$ to 1;
   (2) quantitatively measuring a chemiluminescent signal using HPA (hybridization protection assay), wherein said second unlabeled nucleic acid probe competes with said first nucleic acid probe for said analyte and results in signal quenching by physical reduction in the number of molecules of the first nucleic acid probe bound to the analyte; and
   (3) correlating said chemiluminescence to the presence of said analyte.

* * * * *